(12) United States Patent
Gilton (10) Patent No.: US 7,115,422 B1
(45) Date of Patent: Oct. 3, 2006

(54) SEPARATION APPARATUS INCLUDING POROUS SILICON COLUMN

(75) Inventor: Terry L. Gilton, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 805 days.

(21) Appl. No.: 09/443,070

(22) Filed: Nov. 18, 1999

Related U.S. Application Data (62) Division of application No. 09/177,814, filed on Oct. 23, 1998.

(51) Int. Cl.
   G01N 1/18 (2006.01)

(52) U.S. Cl. ............... 436/178; 435/285.2; 435/286.1; 435/286.5; 435/286.6; 435/287.3; 435/967; 436/514; 436/516; 436/518; 436/34; 436/46; 436/52; 436/151; 436/169; 436/177; 436/825; 422/69; 422/70; 422/99; 422/101; 210/198.2; 210/656; 204/451; 204/601

(58) Field of Classification Search ........... 204/129.55, 204/129.65, 130, 140, 450, 451, 456, 461, 204/468, 601; 210/198.2, 199, 200–207, 210/656–662, 672; 436/7.1, 8, 161, 162, 436/538, 546, 967, 971, 973, 514, 516, 518, 436/34, 46, 52, 151, 169, 177, 825; 438/261; 435/285.2, 286.1, 286.5, 286.6, 287.3, 967, 435/7.1, 8; 422/69, 70, 99, 101

See application file for complete search history.

(56) References Cited

U.S. PATENT DOCUMENTS

| | | | |
|---|---|---|---|
| 4,471,647 A | 9/1984 | Jerman et al. | |
| 4,532,700 A | 8/1985 | Kinney et al. | |
| 4,869,282 A | 9/1989 | Sittler et al. | |
| 4,935,040 A | 6/1990 | Goedert | |
| 5,132,012 A | 7/1992 | Miura et al. | |
| 5,234,594 A | 8/1993 | Tonucci et al. | |
| 5,248,614 A | 9/1993 | Wang | |
| 5,298,767 A | 3/1994 | Shor et al. | |
| 5,340,543 A | 8/1994 | Annino et al. | ........... 422/89 |
| 5,360,759 A | 11/1994 | Stengl et al. | |
| 5,393,401 A | 2/1995 | Knoll | |
| 5,407,534 A | 4/1995 | Thakur | |
| 5,421,958 A | 6/1995 | Fathauer et al. | |
| 5,427,648 A | 6/1995 | Pamulapati et al. | |

(Continued)

OTHER PUBLICATIONS

Stephen C. Terry et al., "A Gas Chromatographic Air Analyzer Fabricated on a Silicon Wafer", IEEE Transactions On Electron Devices, vol. ED-26, No. 12, Dec. 1979, pps. 1880-1886.

*Primary Examiner*—Long V. Le
*Assistant Examiner*—Gailene R. Gabel
(74) *Attorney, Agent, or Firm*—TraskBritt (57) ABSTRACT

A sample separation apparatus including a porous, or rough, capillary column. The porous capillary column includes a matrix which defines pores, and may be formed rough surface of hemispherical grain silicon. The capillary column is defined in a surface of a substrate, such as silicon. The sample separation apparatus may include a stationary phase or a capture substrate disposed on the surfaces thereof. The sample separation apparatus may also include a detector positioned proximate the capillary column. A variation of the sample separation apparatus includes an electrode proximate each end of the capillary column. The sample separation apparatus may be employed to effect various types of chromatographic separation, electrophoretic separation, and analyte identification.

23 Claims, 5 Drawing Sheets

U.S. PATENT DOCUMENTS

| | | |
|---|---|---|
| 5,482,598 A * | 1/1996 | Isaka et al. .................. 204/129 |
| 5,501,787 A | 3/1996 | Bassous et al. |
| 5,508,542 A | 4/1996 | Geiss et al. |
| 5,536,382 A | 7/1996 | Sunzeri |
| 5,571,410 A | 11/1996 | Swedberg et al. |
| 5,583,281 A * | 12/1996 | Yu ........................... 73/23.42 |
| 5,599,759 A | 2/1997 | Inagaki et al. |
| 5,605,662 A | 2/1997 | Heller et al. |
| 5,611,846 A | 3/1997 | Overton et al. ............... 96/102 |
| 5,623,243 A | 4/1997 | Watanabe et al. |
| 5,634,974 A | 6/1997 | Weimer et al. |
| 5,641,400 A | 6/1997 | Kaltenbach et al. |
| 5,663,488 A | 9/1997 | Wang et al. |
| 5,693,946 A | 12/1997 | Vickers et al. |
| 5,721,171 A | 2/1998 | Ping et al. |
| 5,726,085 A | 3/1998 | Crenshaw et al. |
| 5,882,496 A | 3/1999 | Northrup et al. |
| 5,885,869 A | 3/1999 | Turner et al. |
| 5,922,591 A | 7/1999 | Anderson et al. |
| 5,948,227 A | 9/1999 | Dubrow |
| 5,958,791 A | 9/1999 | Roberts et al. |
| 6,126,847 A | 10/2000 | Thakur et al. |
| 6,255,159 B1 | 7/2001 | Thakur |
| 6,379,929 B1 | 4/2002 | Burns et al. |

\* cited by examiner

SEPARATION APPARATUS INCLUDING POROUS SILICON COLUMN

CROSS REFERENCE TO RELATED APPLICATION

This application is a divisional of application Ser. No. 09/177,814, filed Oct. 23, 1998 pending.

BACKGROUND OF THE INVENTION

1. Field of the Invention

The present invention relates to chromatographs and other apparatus for separating the constituents of a sample. Particularly, the present invention relates to a miniaturized separation apparatus which comprises a porous capillary column. More specifically, the porous separation apparatus of the present invention includes a sample column and a detector that is disposed along the column to detect the presence of and identify each constituent that passes by the detector. The porous capillary column may comprise a matrix of porous silicon or hemispherical grain silicon on the surface thereof. The present invention also includes methods for manufacturing and using the inventive separation apparatus.

2. Background of Related Art

Various techniques have long been employed to separate the constituents of a sample in order to facilitate the identification and quantification of one or more of the constituents. Separation techniques are useful for separating inorganic substances and organic substances, such as chemicals, proteins, and nucleic acids. Techniques that have been conventionally employed for separating the constituents of a sample include various types of chromatography and electrophoresis.

Chromatography is a process that is employed in analytical chemistry in order to separate and identify the constituents of a sample. The various types of chromatography that have been conventionally employed include thin layer chromatography (TLC), column chromatography, gel permeation chromatography, ion-exchange chromatography, affinity chromatography, high performance liquid chromatography (HPLC), and gas chromatography (GC).

Thin film chromatography is a well known technique wherein a drop of a sample liquid is applied as a spot to a sheet of absorbent material, which may be paper or a sheet of plastic or glass covered with a thin layer of inert absorbent material, such as cellulose or silica gel. Thin layer chromatographic techniques typically employ a solvent mixture, such as water and an alcohol as respective stationary and mobile phases. The solvent mixture permeates the absorbent material from one edge and the capillary action of the absorbent material moves the sample across the thin layer. One of the solvents binds more tightly to the absorbent material to act as a stationary phase, while the other acts as a mobile phase. As the solvent mixture moves across the absorbent material, the constituents of the sample are separated relative to their solubility in each of the two solvents. Stated another way, the sample constituents equilibrate according to their relative solubilities in each of the solvents. Constituents which are the most soluble in the stationary phase move very little, while constituents which are more soluble in the mobile phase move at higher rates and therefore travel greater distances across the absorbent material.

Conventional column chromatography techniques employ a vertical tube, or column, that is filled with a finely divided solid, or a liquid stationary phase. As a sample is washed down through the stationary phase, it is dissolved in and carried by a mobile phase, which is typically liquid or gas. The various constituents of the sample travel through the stationary phase at different rates. Thus, each of the constituents of the sample spend a different amount of time in the column. The constituents may be collected in fractions as they exit the column and subsequently identified or otherwise analyzed. Constituents of the sample which remain in the stationary phase may be separately identified or otherwise analyzed by sectioning the stationary phase.

Gel permeation chromatography techniques typically employ a column with a stationary phase disposed therein. The stationary phase includes an absorbent gel material with pores of substantially uniform size. As the mobile phase and the sample that is dissolved therein pass through the stationary phase, some of the molecules that are smaller than the pores become entrapped therein, and therefore pass through the column more slowly. The passage of intermediately sized molecules, which are of approximately the same size as the pores, through the column is delayed some, as such molecules enter some of the pores. Molecules that are larger than the pores of the absorbent gel material pass through the stationary phase most quickly, as none of the larger molecules become entrapped in the pores.

Ion exchange chromatography is another variation of column chromatography, wherein the stationary phase comprises positively or negatively charged particles. Oppositely charged constituents of a sample are attracted to the stationary phase, and therefore pass through the column at a slower rate than uncharged constituents and constituents which have the same charge as the charged particles of the stationary phase.

In affinity chromatography, the solid phase comprises particles which have substrate molecules or particles, such as purified antibodies or purified antigens, covalently attached thereto. The substrate binds to a specific constituent or group of constituents in a sample. For example, if the stationary phase comprises antibodies that are specific for a particular antigen, as the sample and mobile phase pass through the column, only that particular antigen will be bound by the stationary phase. The remainder of the sample constituents will pass through the column quickly. The column is subsequently washed to remove any residual amount of the sample from the column. The column is then washed with a dissociating solution, such as a concentrated salt solution, an acidic solution, or a basic solution, in order to dissociate the separated sample constituent from the stationary phase.

High performance liquid chromatography ("HPLC") is similar to column chromatography. In HPLC, the stationary phase is typically a liquid that is carried on very small particles, for example 0.01 mm or less. Consequently, the stationary phase has a very large surface area, and the mobile phase flows extremely slowly therethrough. Thus, a high pressure pump is typically employed in order to increase the rate at which the mobile phase moves through the column.

Conventional gas chromatography methods typically employ a liquid solid phase that is supported by a solid column and a mobile phase that comprises a substantially inert gas, such as nitrogen, argon, hydrogen, or helium. The sample is vaporized as it is injected into the column. As with thin layer chromatography, column chromatography, and HPLC, the constituents of the sample travel across the stationary phase at different rates, and therefore exit the column at different times. As the constituents of the sample exit the column, the constituents are analyzed by a detector, such as a katharometer, a flame ionizer, or an electron capture system, which generates a chromatogram. The identity of each constituent may then be determined by analyzing the chromatogram.

Gas chromatographs are ever-decreasing in size in order to increase their portability. Some small, or miniature or micro gas chromatographs, include columns, which are also referred to as capillary columns, that are fabricated on a silicon substrate. U.S. Pat. No. 5,583,281 (the "'281 patent"), which issued to Conrad M. Yu on Dec. 10, 1996; U.S. Pat. No. 4,935,040 (the "'040 patent"), which issued to Michel G. Goedert on Jun. 19, 1990; and U.S. Pat. No. 4,471,647 (the "'647 patent"), which issued to John H. Jerman et al. on Sep. 18, 1994, each disclose exemplary small silicon gas chromatography columns. The capillary columns that are disclosed in each of the '281, '040, and '647 patents include open channels, or conduits, that are etched into the semiconductor substrate.

Similarly, U.S. Pat. No. 5,132,012 (the "'012 patent"), which issued to Junkichi Miura et al. on Jul. 21, 1992, discloses a liquid chromatograph that includes a capillary column formed in a semiconductor substrate. The capillary column of the chromatograph of the '012 patent comprises an open channel, or conduit.

U.S. Pat. No. 5,571,410 (the "'410 patent"), which issued to Sally A. Swedberg et al. on Nov. 5, 1996, discloses a miniature gas chromatography system which includes a capillary column that is formed in a non-silicon substrate by laser ablation. The capillary column of the chromatograph of the '410 patent comprises an open channel, or conduit, with a substantially smooth surface.

The use of substantially smooth, open-channeled capillary columns in miniature chromatographs is, however, somewhat undesirable from the standpoint that open-channeled columns typically have a surface area that is limited by the area of the substantially smooth surface of the channel. The amount of stationary phase material that may be disposed along a given length of substantially smooth, open-channeled capillary columns is also limited by the surface area of that length of the capillary column. Thus, in order to effectively separate the various constituents of a sample, the capillary column must be relatively long. Consequently, the substrate on which the capillary column is formed must have a sufficient surface area to facilitate fabricating the capillary column thereon. Thus, the use of substantially smooth, open-channeled capillary columns in miniature gas chromatographs imposes minimum size limitations on such chromatographs.

Another technique for separating the various constituents of a sample is typically referred to as electrophoresis. Electrophoresis is a process whereby molecules having a net overall electrical charge are migrated at a rate that depends on the electrical charge, size and shape of the molecule. Electrophoresis techniques typically employ a solid matrix through which the constituents, or molecules, of the sample are migrated. A variation of electrophoresis that is typically referred to as polyacrylamide gel electrophoresis (PAGE) separates molecules based strictly on their size. In PAGE, the molecules of the sample are typically linearized and separated, or disassociated from themselves and from other molecules, by means of sodium dodecyl sulfate (SDS), a detergent that binds to the hydrophobic regions of proteins, and 2-mercaptoethanol, or β-mercaptoethanol, which breaks disulfide (S—S) linkages that occur between some amino acids of a protein. The sample is then migrated through a polyacrylamide gel cross-linked matrix, which has very small pores. The pore size of the polyacrylamide gel may be adjusted in accordance with the molecular size, or weight, range for which separation is desired.

The preparation of polyacrylamide gels is a relatively long process. Moreover, the acrylamide that is used to form the gel matrix is a neurotoxin. Some of the other chemicals that may be utilized in electrophoretic processes are also hazardous. In addition, the amount of electric current that may be used to separate the constituents of a sample in gel electrophoresis has conventionally been limited, as too great a current will melt or otherwise disrupt the structure of the gel.

Thus, a small separation apparatus is needed that may be employed to conduct various types of sample separation, which is smaller than conventional devices, and which separates samples adequately. There are also needs for reduced equipment and operational costs.

SUMMARY OF THE INVENTION

The separation apparatus, method of manufacturing the separation apparatus, and methods of using the separation apparatus of the present invention address each of the foregoing needs.

The sample separation apparatus of the present invention includes a substrate with a capillary column thereon, the latter comprising a rough surface, such as a matrix which defines a plurality of pores therethrough or an open column with a rough surface, which is also referred to as a matrix. The surface area of the matrix of each capillary column facilitates the separation of the constituents of a sample over a relatively short length of the column compared to the required lengths of conventional smooth, "open," etched or ablated columns to effectively separate the constituents. Preferably, the capillary column, which is also referred to as a porous capillary column, comprises porous silicon or hemispherical grain silicon, and is formed on a silicon substrate. Such a column, depending on the width and depth thereof, may be useful for separating the constituents of a sample or detecting constituents in a sample having a volume of as small as about one femtoliter ($1 \times 10^{-15}$ liter). The separation apparatus may also include a detector disposed proximate the capillary column. Such a detector analyzes a characteristic of a constituent as the constituent passes through the capillary column, and thereby identifies or otherwise analyzes the constituent.

In a first variation of the apparatus of the present invention, the sample separation apparatus may be employed as a chromatography column. Accordingly, a stationary, or solid, phase is disposed on the matrix of the capillary column. The type of stationary phase that is selected for use in the sample separation apparatus is dependent upon several factors, including without limitation the chromatographic technique that will be employed with the separation apparatus and the type of sample constituents that are to be isolated. The types of stationary phase materials that are useful in conventional chromatographic processes are also useful in the first variation of the separation apparatus.

A second variation of the separation apparatus of the present invention is useful for conducting electrophoretic separation. Thus, size of the pores that are defined through the porous silicon matrix or the amount of space between grains of hemispherical grain silicon of the capillary column is determined by the desirable rate of separation and the size of the sample constituents for which separation is desired. The second variation of the separation apparatus also includes first and second electrodes positioned proximate respective first and second ends of the capillary column. The first and second electrodes are connectable to opposite electrical charges so as to facilitate the generation of a current along a length of the capillary column, and thereby facilitate the movement and separation of the sample constituents along the column. Preferably, the second variation of the separation apparatus also includes a control column adjacent the capillary column and having substantially the same dimensions, structure, and pore sizes or spacing as the capillary column. The control column is useful for determining the molecular size or weight of at least some of the various sample constituents.

In a third variation of the apparatus, the sample separation apparatus may be employed to detect the presence or absence of increased levels of a certain analyte. Accordingly, the third variation includes a capture substrate disposed on at least a portion of the rough surfaces of the capillary column. Preferably, the capture substrate has a specific affinity for the measured, or assayed, analyte.

A method of fabricating the sample separation apparatus of the present invention includes selectively forming a capillary column in a substrate.

When a silicon substrate is employed, various techniques which are known in the art may be employed to define a porous silicon capillary column therein. Known techniques may also be used in order to form pores of a desired size. Known semiconductor layer formation processes may also be employed to fabricate a detector proximate the capillary column. Similarly, known processes are useful for fabricating electrodes and other structures upon a surface of the substrate.

Capillary columns that include hemispherical grain silicon may also be selectively formed in a substrate by known techniques. First, a trench, which defines the path of the capillary column, is defined in a substrate by known patterning processes, such as mask and etch techniques. The surface area of the surfaces of the trench may then be increased by known methods, such as by forming hemispherical grain silicon thereon.

A method of utilizing the inventive separation apparatus includes disposing a sample proximate an end of the porous capillary column and drawing the sample through the porous capillary column to generate a flowfront of the sample and effect the separation of a constituent from the sample. The sample may be drawn along the capillary column by positive pressure, negative pressure, capillary action, electric current, or any other known technique that is employed to facilitate the movement of a sample along a separation apparatus.

Variations of the inventive method employ the separation apparatus of the present invention to effect various separation techniques, including, without limitation, various types of chromatographic separation, electrophoresis, and the isolation and detection of one or more analytes from a sample.

Other advantages of the present invention will become apparent to those of ordinary skill in the relevant art through a consideration of the appended drawings and the ensuing description.

DETAILED DESCRIPTION OF THE INVENTION

Figure 1:
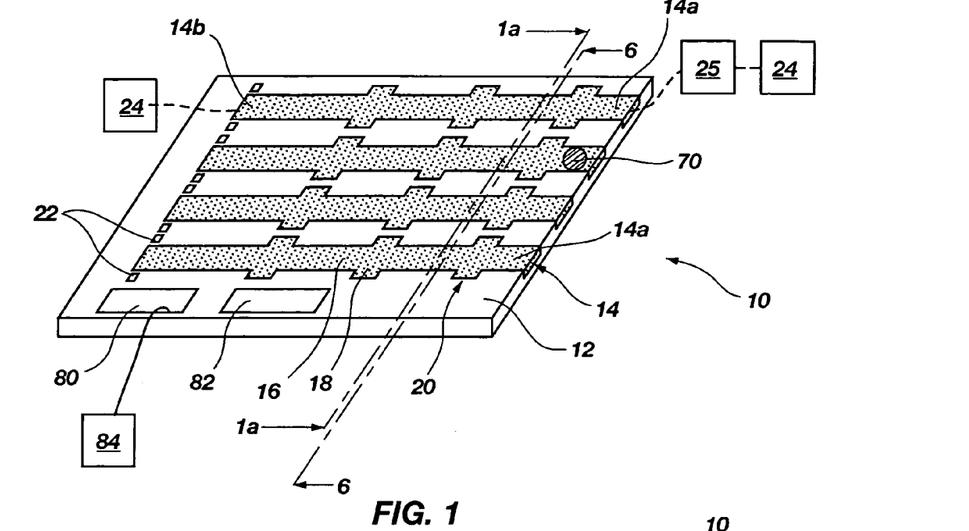
FIG. 1 is a perspective view of an embodiment of a sample separation apparatus of the present invention.

With reference to FIG. 1, a first embodiment of a sample separation apparatus 10 of the present invention is depicted. Sample separation apparatus 10 includes a substrate 12 and capillary columns 14 formed in the substrate. Capillary columns 14 each include a matrix 16 and a plurality of pores 18 formed through the matrix. Pores 18 permit gases and liquids to flow along the distance of capillary columns 14. Capillary columns 14 may also include one or more reaction regions 20 along the longitudinal extent thereof. Preferably, the reaction regions 20 along each capillary column 14 are discrete from one another. Sample separation apparatus 10 may also include one or more detectors 22 disposed proximate each capillary column 14.

Substrate 12 may be formed of silicon, gallium arsenide, indium phosphide, or another material that can be treated to form porous regions, such as capillary columns 14, and upon which electrical devices, such as detector 22, can be formed. Accordingly, capillary columns 14 may each comprise porous silicon.

Alternatively, capillary columns 14 may be etched into a surface of substrate 12, and the surfaces of capillary columns 14 roughened. An exemplary means of roughening the surfaces of capillary columns 14 includes forming hemispherical grain silicon thereon.

FIG. 1 illustrates a sample separation apparatus 10 that includes four capillary columns 14. The length and porosity of each column 14 depends, in part, upon the surface tension and viscosity of the sample to be measured, and the desired degree of separation. As depicted, each capillary column 14 includes three reaction regions 20. Preferably, variations of sample separation apparatus 10 with more than one capillary column 14 include an equal number of reaction regions 20 along each capillary column. Moreover, in variations of sample separation apparatus 10 wherein the capillary columns 14 each include more than one reaction region 20, the positioning and spacing between corresponding reaction regions are preferably substantially the same along each of the capillary columns. Preferably, corresponding reaction regions 20 on different columns 14 have substantially the same dimensions and pores 18, or spacing between adjacent grains of hemispherical grain silicon, which spaces are also referred to as "pores," of substantially the same sizes and porosity.

Pores 18 may have cross-sectional diameters ranging from about one nanometer (1 nm) or less to about 100 nm or greater. Due to the small size of pores 18, the surface tension of many liquid samples will cause such samples to travel very slowly along the distance of capillary column 14 and create a flowfront. Gaseous samples typically do not exhibit capillary action; thus, some amount of force is required to facilitate the movement of gaseous samples along capillary column 14. Accordingly, a migration facilitator 24, such as a pump, vacuum, or current-generating device, which is also referred to as a flow facilitator, may be disposed proximate capillary column 14 in order to facilitate or increase the migration rate of a sample 70 therealong.

Detectors 22 may be disposed adjacent capillary column 14 in order to identify or otherwise analyze a constituent of sample 70 as the constituent passes thereby. Various embodiments of detector 22 include, but are not limited to, thermistors, field effect transistors (FETs) that are capable of sensing various types of chemicals, components that measure current as a voltage is applied to sample 70, and other devices that are known to measure at least one characteristic of a constituent of sample 70 or otherwise facilitate identification of the constituent. U.S. Pat. No. 5,132,012 (the "'012 patent"), which issued to Junkichi Miura et al. on Jul. 21, 1992, the disclosure of which is hereby incorporated by reference in its entirety, discloses an exemplary field effect transistor that may be employed as a detector 22 in the present invention. U.S. Pat. No. 4,471,647 (the "'647 patent"), which issued to John H. Jerman et al. on Sep. 18, 1984, the disclosure of which is hereby incorporated by reference in its entirety, discloses an exemplary thermal detector that may be employed as a detector 22 in the sample separation apparatus of the invention. Detector 22 may be positioned proximate an exit end 14b, which is also referred to as a second end, of capillary column 14 to analyze the various constituents of sample 70 as they pass thereby. Alternatively, as shown in FIG. 1b, detector 22 may be positioned proximate a reaction region 20 of capillary column 14. More than one detector 22 may be disposed proximate each capillary column 14 to analyze sample 70 and the constituents thereof at various positions of the capillary column.

Separation apparatus 10 may also include a processor 80 and a memory device 82, each of a type known in the art. Processor 80 receives information about sample 70, or "sample information," from one or more types of detectors 22 along column 14 and processes the sample information to output same in a user-friendly format to a display 84 external of sample separation apparatus 10. In processing the sample information, processor 80 may compare the sample information to known information that has been stored in memory device 82, and thereby identify the sample or generate other data regarding the sample information. The sample identity may then be transmitted to display 84. Following the comparison of sample information to known information, processor 80 may direct memory device 82 to store information about the sample, including its identity and associated data.

Figure 1A:
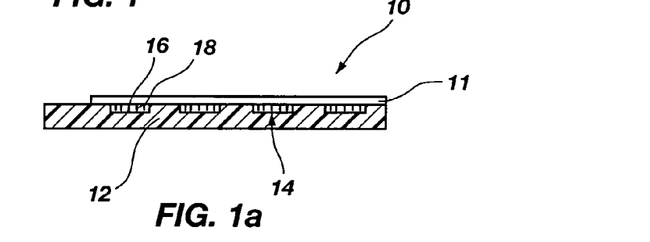
FIG. 1a is a cross-section taken along line 1a—1a of FIG. 1, which also illustrates a sealing element disposed over at least a portion of the sample separation apparatus.
Figure 1B:
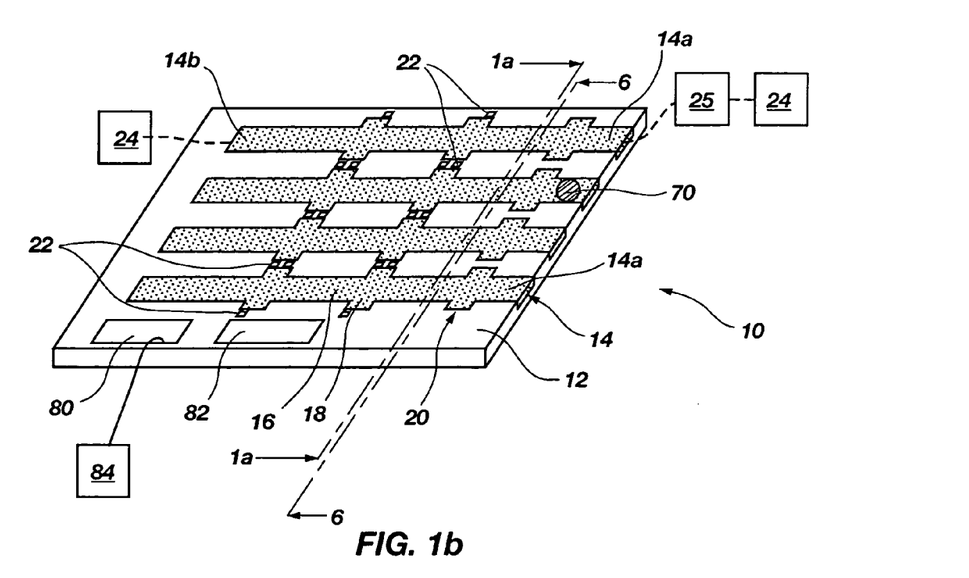
FIG. 1b is a perspective view of a variation of the sample separation apparatus of FIG. 1, which illustrates an alternative placement of detectors.

With reference to FIG. 1a, separation apparatus 10 may also include a sealing element 11 disposed over a substantial portion of the area of each capillary column 14 that is exposed on substrate 12. Sealing element 11 is preferably electrically insulative and may be manufactured from silicon dioxide, glass (e.g., borosilicate glass (BSG), phosphosilicate glass (PSG), borophosphosilicate glass (BPSG), etc.), silicon nitride, polyimide, other electrically non-conductive polymers, or any other electrically insulative material.

Figure 2:
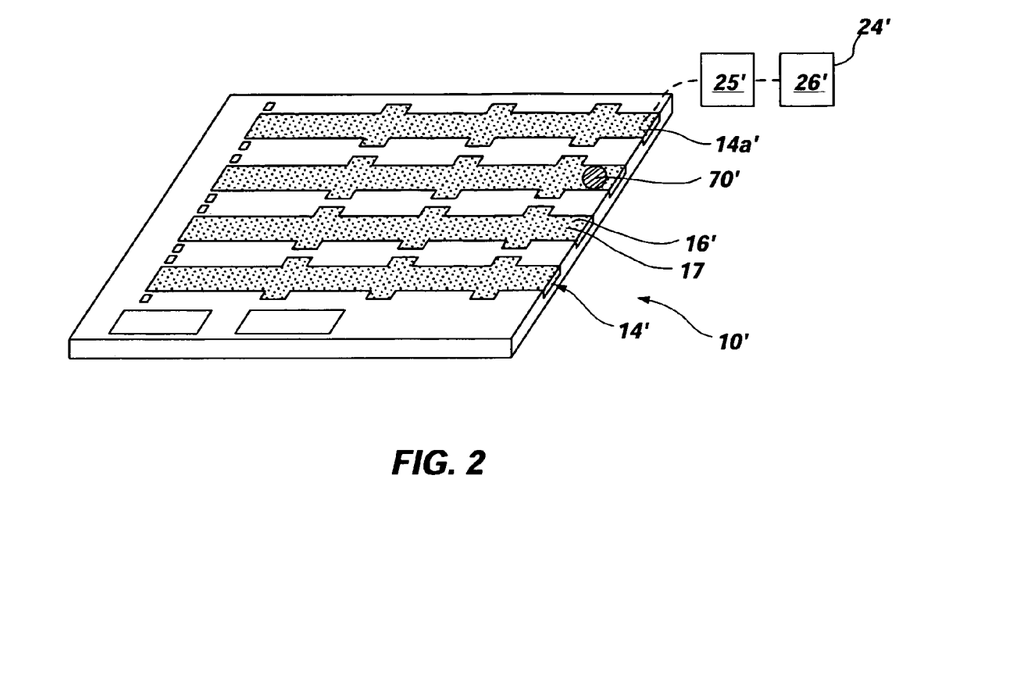
FIG. 2 is a perspective view of a variation of the sample separation apparatus of FIG. 1 that is useful for performing chromatography.

Turning now to FIG. 2, a second embodiment of the sample separation apparatus 10' of the present invention is shown, which comprises a chromatography column. Accordingly, a stationary phase 17 may be disposed on matrix 16' of each capillary column 14'. Stationary phase 17 comprises a material that is selected on the basis of several factors, including without limitation the chromatographic technique that will be employed and type of sample constituents for which separation or isolation is desired. Conventionally employed stationary phase materials may also be employed as stationary phase 17.

Separation apparatus 10' may also include a migration facilitator 24' which comprises a pump 26' that applies positive pressure to facilitate the migration of a sample along each capillary column 14'. Exemplary pumps 26' that are useful in separation apparatus 10' are disclosed in U.S. Pat. No. 5,663,488 (the "'488 patent"), which issued to Tak Kui Wang et al. on Sep. 2, 1997, the disclosure of which is hereby incorporated by reference in its entirety. Preferably, pump 26' is positioned proximate a sample application end 14a', or first end, of each capillary column 14', and is in flow communication with the capillary column and to facilitate movement of a sample 70' along each column 14'. A valve 25' may be disposed between pump 26' and each column 14' in order to control the volume of gas or liquid that is forced into the column by the pump in order to apply pressure to the column. Exemplary valves 25' that are useful in the separation apparatus of the present invention include the valves that are disclosed in U.S. Pat. Nos. 4,869,282 (the "'282 patent"), which issued to Fred C. Sittler et al. on Sep. 26, 1989, and U.S. Pat. No. 5,583,281 (the "'281 patent"), which issued to Conrad M. Yu on Dec. 10, 1996, the disclosures of each of which are hereby incorporated by reference in their entirety.

Figure 2A:
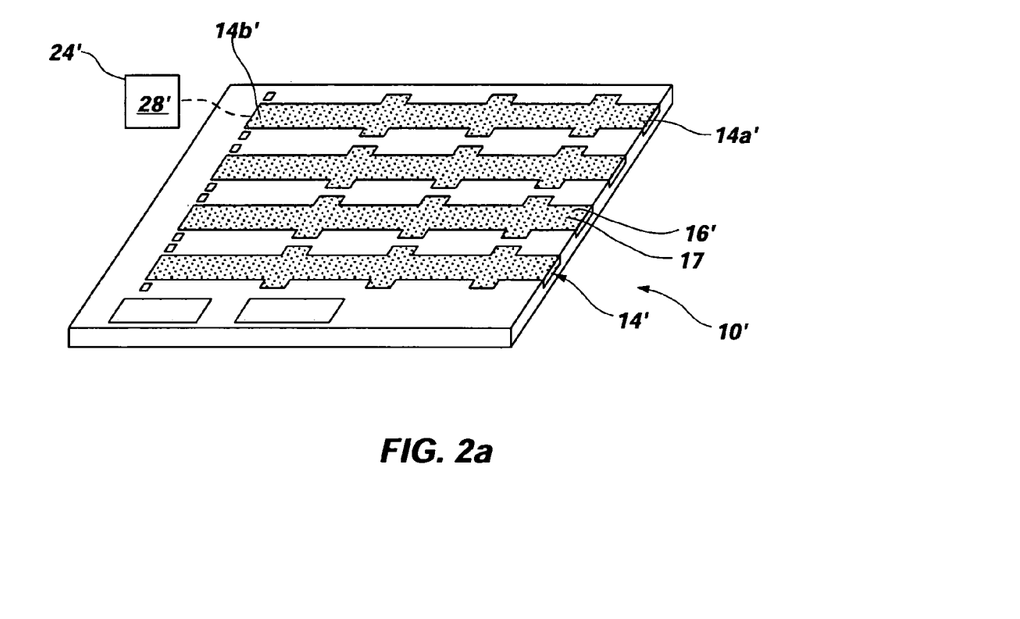
FIG. 2a is a perspective view of a variation of the sample separation apparatus of FIG. 2 including a vacuum source operatively connected to the capillary column.

Alternatively, as depicted in FIG. 2a, migration facilitator 24' may comprise a vacuum source 28', as known in the art, which exerts a negative pressure on sample 70' in order to pull the sample along each capillary column 14'. Such a vacuum source is operatively attached to capillary column 14', and in flow communication therewith, proximate an exit end 14b', or second end, thereof. Preferably, the amount of negative pressure that is generated by vacuum source 28' and applied to each capillary column 14' may be adjusted or varied.

Figure 3:
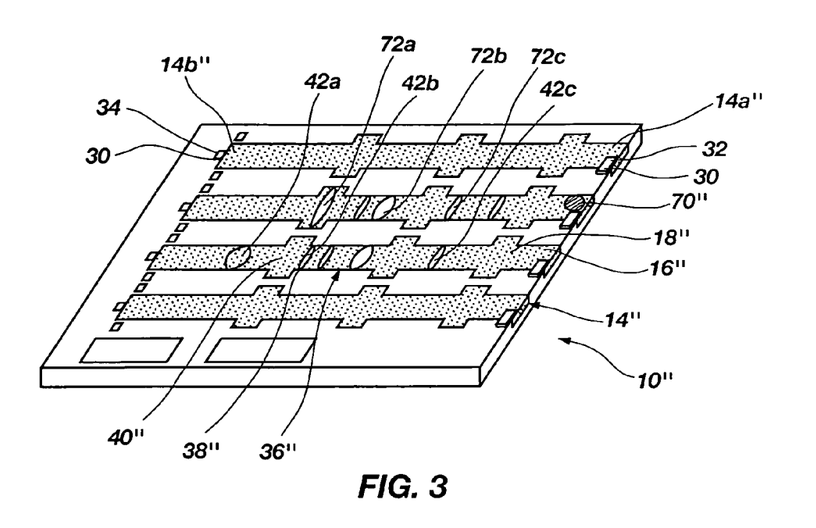
FIG. 3 is a perspective view of another variation of the sample separation apparatus of FIG. 1 that is useful for performing electrophoresis.

FIG. 3 illustrates a third embodiment of the sample separation apparatus 10" of the present invention, which is particularly useful for conducting electrophoretic separation on a sample 70". The degree to which the constituents of sample 70" are separated depends upon the cross-sectional diameter of pores 18". Accordingly, the greatest degree of separation occurs when the size of pores 18" is approximately equivalent to the size of the various constituents of sample 70" for which separation is desired, or the "targeted" constituents. Thus, pores 18" of small cross-sectional diameters separate the smaller constituents of sample 70". Pores 18" of larger cross-sectional diameters permit the migration and separation of the larger sized constituents through each capillary column 14". Thus, the cross-sectional diameter of pores 18" preferably facilitates separation of the various targeted constituents of sample 70".

Electrophoretic techniques typically employ an electric current to move the constituents of sample 70". Thus, sample separation apparatus 10" may include a migration facilitator that comprises an electric current-generating component 30. Current-generating component 30 includes a first electrode 32 disposed proximate a sample application end 14a", which is also referred to as a first end, of each capillary column 14", and a second electrode 34 that is positioned proximate exit end 14b" of each capillary column 14". First and second electrodes 32 and 34, respectively, are fabricated from an electrically conductive material, and are connectable to opposite electrical charges so as to facilitate the generation of a current along a length of the capillary column. Thus, first and second electrodes 32 and 34, respectively, facilitate the migration of the constituents of sample 70" along their respective capillary columns 14" and the separation of the constituents during migration.

Figure 3A:
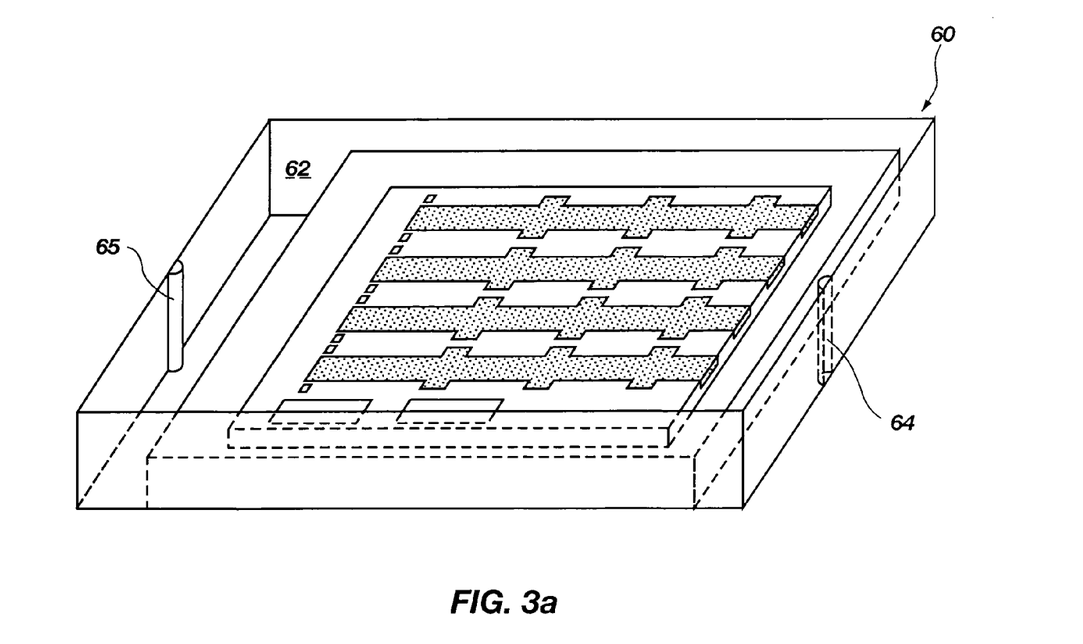
FIG. 3a is a schematic representation of the sample separation apparatus of FIG. 3, illustrating use of the sample separation apparatus in association with an electrophoresis apparatus.

Alternatively, with reference to FIG. 3a, a sample separation apparatus 10" which lacks a current-generating component may be utilized in association with a conventional electrophoresis apparatus 60 that includes a chamber 62 with a cathode 64 extending into one end thereof and an anode 65 extending into an opposite end of the chamber.

Referring again to FIG. 3, separation apparatus 10" also includes a control column 36" adjacent at least one of capillary columns 14", which has substantially the same dimensions and a matrix 38" and pores 40" having substantially the same configurations and sizes as the matrix 16" and pores 18" of each capillary column 14". Control column 36" is useful for separating a control which includes markers 42a, 42b, 42c, etc. of known molecular size and weight. Thus, as is known in the art, at least some of the various constituents of the sample may be compared to markers 42a, 42b, 42c, etc. in order to approximate the molecular size or weight of these constituents.

Figure 4:
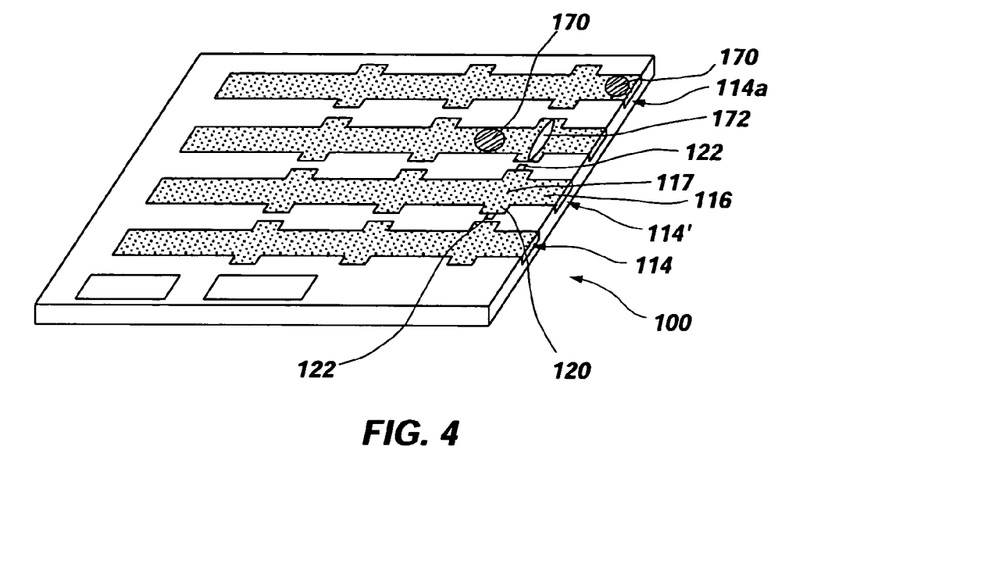
FIG. 4 is a perspective view of another variation of the sample separation apparatus of FIG. 1 that is useful for isolating and detecting an analyte.

Referring now to FIG. 4, a fourth embodiment of the sample separation apparatus 100 of the present invention is illustrated. Separation apparatus 100 includes a stationary phase, which is referred to as capture substrate 117, which detects the presence and approximate levels of a particular analyte or group of analytes in the sample. Capture substrate 117 may include an antibody, an antigen, or any other substrate material which separates a constituent from a sample on the basis of affinity for the constituent. Accordingly, sample separation apparatus 100 comprises an assay device. Preferably, capture substrate 117 has a specific affinity for the detected analyte or group of analytes. Capture substrate 117 is disposed along a portion of each capillary column 114 and securely bound to matrix 116 so as to retain substantially all of the capture substrate on the matrix as a sample passes thereby. Capture substrate 117 is preferably bound to matrix 116 at reaction region 120. Accordingly, detector 122 is preferably positioned proximate reaction region 120 in order to detect whether or not capture substrate 117 has bound an analyte.

Figures 5, 6:
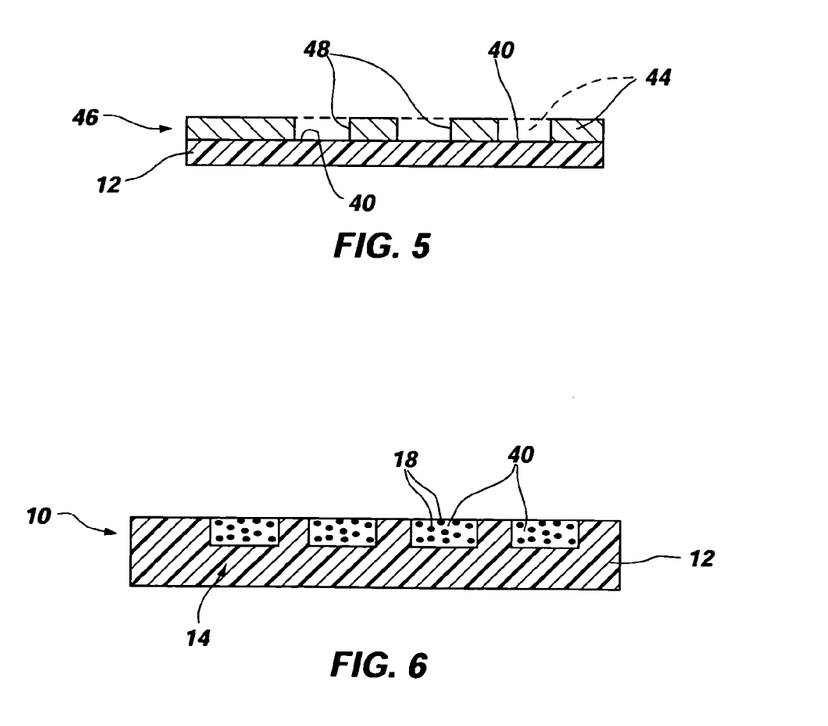
FIG. 5 is a cross-sectional view of a substrate that has been patterned to define capillary column regions thereon.
FIG. 6 is an enlarged cross-sectional view taken along line 6—6 of FIG. 1 and illustrating the capillary columns.
Figure 7:
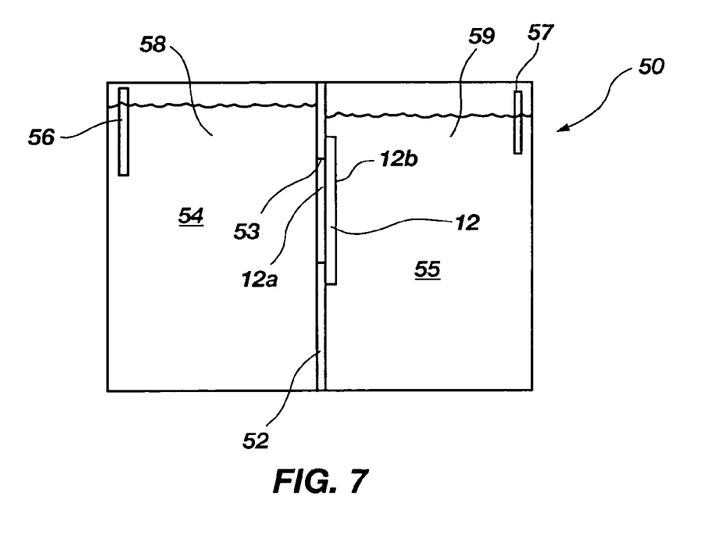
FIG. 7 is a schematic representation of the use of an anodization chamber to porify the capillary column regions of the substrate of FIG. 5.

Referring again to FIG. 1, capillary columns 14 may be formed upon substrate 12 by processes that are known in the art, including processes for forming porous silicon from silicon. FIGS. 5 through 7 illustrate an exemplary process for fabricating sample separation apparatus 10. With reference to FIG. 5, substrate 12 is appropriately patterned to define the desired number and shapes of capillary column regions 40. As shown in FIG. 6, pores 18 are then created in the defined capillary column regions 40, which is also referred to as "porifying" of the capillary column regions, by techniques that are known in the art, such as anodization in the presence of hydrofluoric acid (HF).

Referring again to FIG. 5, patterning may include masking and etching techniques that are known in the art, such as those in which photoresists are employed. A photoresist 44 is disposed over the surface of substrate 12 and defined by photolithography processes, as known in the art, to define a mask 46 with openings 48 therethrough. Openings 48 expose various areas of substrate 12, which are referred to as capillary column regions 40.

Patterning may also include the doping of substrate 12 with dopants and by techniques that are known in the art in order to provide the desired amount of porosity and porous silicon of a desired morphology. As those in the art are aware, the ability to form pores in silicon by anodization processes, as well as the size and density of such pores and the rate at which pores are formed, depend upon the presence or absence of dopant and the type and concentration of dopant. For example, small pores may be formed in P-doped silicon. Larger pores are more readily formed in P+doped silicon. N+doped silicon typically resists the formation of pores by anodization. Accordingly, patterning may also include repeated masking and differential doping of substrate 12 in order to facilitate the subsequent selective creation of a porous matrix through the substrate. Such doping processes are disclosed in U.S. Pat. No. 4,532,700 (the "'700 patent"), which issued to Wayne I. Kinney et al. on Aug. 6, 1985, and U.S. Pat. No. 5,360,759 (the "'759 patent"), which issued to Reinhard Stengl et al. on Nov. 1, 1994, the disclosures of both of which are hereby incorporated by reference in their entirety.

Alternatively, patterning may include a mask and etch, as known in the art, followed by damaging, or "roughing," the exposed areas of substrate 12 to define capillary column regions 40, as disclosed in U.S. Pat. No. 5,421,958 (the "'958 patent"), which issued to Robert W. Fathauer et al. on Jun. 6, 1995, the disclosure of which is hereby incorporated by reference in its entirety. It is known in the art that porous silicon forms more readily on damaged, or roughened, areas on the surface of a silicon substrate 12. As the '958 patent discloses, the damaging of substrate 12, or the creation of imperfections on same, may include, without limitation, mechanically damaging substrate 12 and applying energetic beams to substrate 12.

FIG. 7 schematically illustrates an anodization chamber 50 in which an exemplary process for porifying capillary column regions 40 of substrate 12 (see FIG. 6) may occur. The porifying of capillary column regions 40 in order to define capillary columns 14 (see FIGS. 1 and 6) in substrate 12 may be performed by conventional processes, including processes for forming porous silicon regions in semiconductor devices. Exemplary process for forming porous silicon from a silicon substrate are disclosed in each of the '700, '759, and '958 patents. Such porification processes typically include positioning substrate 12 within an anodization chamber 50, adjacent a partition 52, which separates the anodization chamber into a first cell 54 and a second cell 55, which are also referred to as "sections." An anode 56 extends into first cell 54. Similarly, a cathode 57 extends into second cell 55. Partition 52 includes an opening 53 therethrough, which is covered by substrate 12 and sealed to prevent the passage of liquids between first cell 54 and second cell 55. Thus, an upper surface 12a of substrate 12 is exposed to first cell 54, while an opposing base surface 12b is exposed to second cell 55. First cell 54 is filled with an anodizing solution 58, such as concentrated hydrofluoric acid, while second cell 55 is filled with an electrically conductive liquid 59, such as 50% isopropyl alcohol. By means of anode 56 and cathode 57, an electric current is then applied to anodization chamber 50. As current passes through substrate 12, the areas of upper surface 12a that are exposed to first cell 54 become porous.

The size of pores 18 is determined by, and may be varied by, varying several factors, including, without limitation, the concentration of any doped regions of the substrate, the presence or absence of dopants, the type of dopants, the relative concentrations of the various elements of the anodizing solution, the duration of exposure to the anodizing solution, the current density, the illumination, and the temperature of the anodizing solution.

Other known processes for patterning capillary column regions 40 on substrate 12 and porifying same, such as that disclosed in U.S. Pat. No. 5,599,759 (the "'759 patent"), which issued to Shinji Inagaki et al. on Feb. 4, 1997, the disclosure of which is hereby incorporated by reference in its entirety, are also useful for defining capillary columns 14 on substrate 12, and are therefore within the scope of the fabrication process of the present invention.

Figure 8:
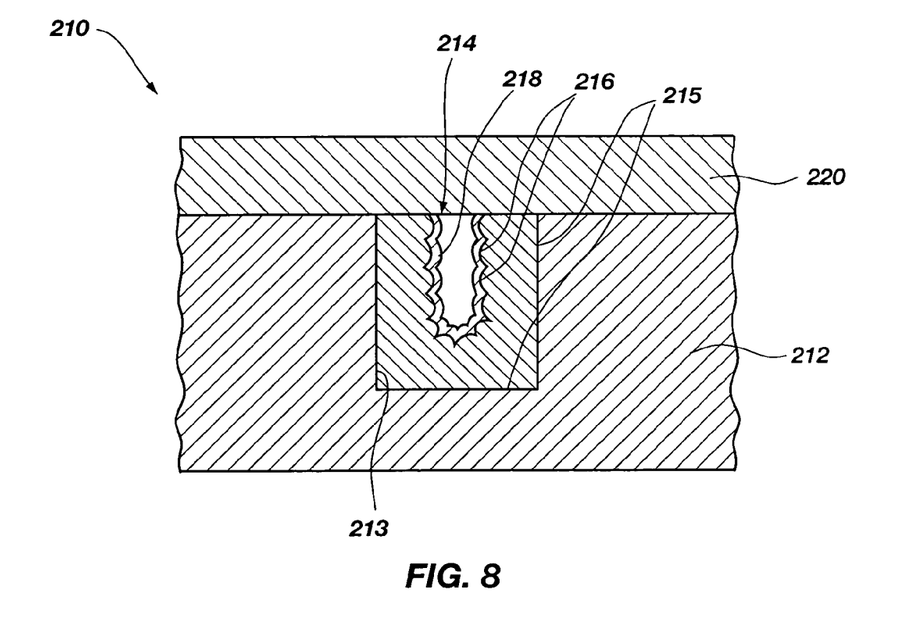
FIG. 8 is an enlarged cross-sectional view of an alternative rough capillary column, which includes hemispherical grain silicon on the surface thereof.

With reference to FIG. 8, as another alternative, capillary columns 214 that include hemispherical grain silicon 216 on the surfaces 215 thereof may be formed in selected regions of a substrate 212 by known techniques. First, an elongate trench 213, which defines the path of the capillary column, is defined in a substrate by known patterning processes, such as mask and etch techniques. The area of the surfaces of trench 213 may then be increased by known methods, such as by forming hemispherical grain silicon 216 thereon. Exemplary methods of forming hemispherical grain silicon that may be employed to fabricate capillary columns 214 include those disclosed in U.S. Pat. No. 5,407,534, which issued to Randhir P. S. Thakur on Apr. 18, 1995; U.S. Pat. No. 5,623,243, which issued to Hirohito Watanabe et al. on Apr. 22, 1997; U.S. Pat. No. 5,634,974, which issued to Ronald A. Weimer et al. on Jun. 3, 1997; U.S. Pat. No. 5,721,171, which issued to Er-Xuan Ping et al. on Feb. 24, 1998; and U.S. Pat. No. 5,726,085, which issued to Darius Lammont Crenshaw et al. on Mar. 10, 1998, the disclosures of each of which are hereby incorporated by reference in their entirety. In general, a film of amorphous silicon is formed in trench 213. Impurities are then seeded into the amorphous silicon. Then, the material is annealed to cause nucleation sites to grow at the seeding sites to thereby form the rough textured hemispherical grain silicon 216. A solid phase 218, such as a native oxide layer, may then be grown on the surface of the hemispherical grain silicon 216. Finally, the entire structure 210 may be enclosed by a cover layer 220 or a suitable package.

The hemispherical grain silicon 216 provides a rough texture on the interior surface of the capillary column 214. The surfaces 215 of capillary column 214 are characterized by hemispherical or mushroom-shaped bumps, which form a porous, matrix-like structure. The hemispherical grain silicon 216 provides at least about 1.6 to 2.2 times the surface area that would otherwise be provided by a conventional surface etched in silicon. Silicon oxide may be employed as solid phase 218. Silicon oxide is a suitable solid phase material for separating or detecting a wide variety of materials. Alternatively, materials with different absorption characteristics, such as suitable resins, metals, or metal oxides, may be employed as solid phase 218.

Referring again to FIGS. 1–1b, detector 22, processor 80, memory device 82, valves 25, first electrode cathode 32 (FIG. 3), or second electrode or anode 34 (FIG. 3) and other components that are carried upon substrate 12 may be fabricated upon the substrate in a desired location by known semiconductor fabrication processes. Such semiconductor fabrication processes include, without limitation, layer deposition processes (e.g., sputtering and chemical vapor deposition); oxidation processes; patterning processes (e.g., masking and etching); and other conventional semiconductor device fabrication processes.

A stationary phase (see FIGS. 1 through 4) may be applied to matrix 16 as known in the art.

With continued reference to FIG. 1, a method of utilizing the inventive sample separation apparatus 10 includes disposing a sample proximate first end 14a of at least one capillary column 14. A liquid sample 70 may then be drawn along the length of capillary columns 14 by capillary action or with the assistance of migration facilitator 24. A gaseous sample 70 may be drawn along the length of capillary column 14 by means of migration facilitator 24. As sample 70 is drawn through pores 18 that are defined by matrix 16, one or more constituents of sample 70 is separated from the remainder of sample 70. The mechanism by which the separation of a constituent from sample 70 occurs depends upon the separation technique that is performed, as explained in greater detail below. The separated constituents may then be detected when they are in close proximity to, or proximate, a detector 22.

Referring again to FIGS. 2 and 2a, when sample separation apparatus 10' is employed in a chromatographic technique, one or more constituents of a sample 70' are separated in accordance with their relative solvencies in stationary phase 17, which is disposed on matrix 16', and a mobile phase, which carries the sample along the length of each capillary column 14'. When either gas chromatography or HPLC is performed, the use of a pump 26' (see FIG. 2) or a vacuum source 28' (see FIG. 2a) is preferred in order to facilitate the migration of the sample along each capillary column 14'. Pump 26' or vacuum source 28' may also be employed to facilitate sample migration along capillary columns 14' during the use of sample separation apparatus 10' to perform other chromatographic techniques.

Turning again to FIG. 3, in order to separate one or more constituents of a sample 70" by electrophoresis, the sample is first dissolved in a conventional carrier solvent, which typically includes a pH buffer solution of a desired pH, 2-mercaptoethanol, SDS, and glycerol. The SDS imparts the constituents of sample 70" with a negative net charge and facilitates the unraveling, or linearization, of the constituents. The 2-mercaptoethanol breaks covalent disulfide (S—S) bonds between some amino acids of some protein constituents.

With continued reference to FIG. 3, a first variation of the electrophoretic method of the present invention includes applying sample 70" to first end 14a" of at least one capillary column 14". Preferably, sample 70" is diluted in a pH-buffered solution, as known in the art. An electric current is then applied to current-generating component 30, in order to migrate sample 70" along capillary columns 14". Preferably, first electrode 32 acts as a cathode (i.e., electrons flow therefrom), while second electrode 34 acts as an anode (i.e., electrons flow thereto).

Alternatively, with reference to FIG. 3a, a second variation of the electrophoretic method according to the present invention is illustrated, wherein sample separation apparatus 10" may be disposed in an electrophoresis apparatus 60 of the type that is typically employed in gel electrophoretic techniques. Electrophoresis apparatus 60 includes a chamber 62 with a cathode 64 extending into one end thereof, and an anode 65 extending into the opposite end thereof. A buffer solution of any of the types that are typically employed in electrophoresis, and having a desired pH, is poured into chamber 62. Sample separation apparatus 10" is then positioned in electrophoresis apparatus 60, with first end 14a" of capillary columns 14" proximate cathode 64 and second end 14b" proximate anode 65. A sample 70" is applied to first end 14a", and an electric current of desired amperage is then applied to cathode 64 and anode 65 in order to migrate the sample along the length of at least one capillary column 14".

In both the first and second variations of the electrophoretic method of the present invention, as the sample migrates through pores 18, the constituents 72a", 72b", 72c", etc. of sample 70" may be separated on the basis of size or net electric charge. When separation of constituents 72" on the basis of size is desired, sample 70" preferably includes a substance, such as SDS, which imparts each of constituents 72" with the same net electrical charge. Various constituents of the sample may then be detected with a detector, by staining, spectrophotometrically, radiographically, or by other detection or identification techniques that are known in the art.

As an example of the use of sample separation apparatus 100, which is illustrated in FIG. 4, a constituent, or an "analyte" 172, of a sample 170 is isolated from the remainder of the sample. Sample 170 is applied to first end 114a of at least one capillary column 114. As sample 170 moves through column 114, each of the constituents of the sample, including analyte 172, contact capture substrate 117. If sample 170 includes any analytes 172 for which capture substrate 117 has an affinity, these analytes are bound by the capture substrate 117 and isolated from the remainder of the sample as the sample contacts and passes by the capture substrate. The presence or absence of capture substrate 117-bound analytes 172 may then be detected by detector 122, by staining, spectrophotometrically, radiographically, or by other detection or identification techniques that are known in the art. The concentration or relative amounts of each isolated analyte 172 may also be determined in such a manner.

As another example of the use of sample separation apparatus 100, to detect the presence of silver, capillary column 114 may be provided with a free chloride source, such as calcium chloride or sodium chloride. When an aqueous solution containing silver is drawn into the capillary column 114, resultant precipitation of silver chloride would reduce the chloride concentration in capillary column 114. The resultant reduced ionic conductivity in capillary column 114 may be measured by detector 122 and compared to a conductivity profile stored in a memory element associated with sample separation apparatus 100. For the purpose of comparison, another capillary column 114' of sample separation apparatus 100 may be provided with no free chloride source. As the aqueous silver solution is drawn into the second capillary column 114', the ionic conductivity of the second capillary column 114' may be measured by another detector. The ionic conductivity profile of the second capillary column 114' may be compared to that of the first capillary column 114 and to the conductivity profile. The measured and stored data may then be processed to determine the concentration of silver in the original sample.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. The scope of this invention is, therefore, indicated and limited only by the appended claims and their legal equivalents, rather than by the foregoing description. All additions, deletions and modifications to the invention as disclosed herein which fall within the meaning and scope of the claims are to be embraced within their scope.

What is claimed is:

1. A method of substantially isolating a constituent of a sample, comprising: dispersing the sample in a mobile phase;

applying the sample to a first end of a porous capillary column formed in a nonporous substrate, said porous capillary column comprising a matrix including the same material as said nonporous substrate and at least one capture substrate disposed on said matrix; and drawing the sample across a flowfront through said porous capillary column so as to enhance separation of the constituent from the sample by said at least one capture substrate.

2. The method of claim 1, further comprising detecting the constituent with at least detector disposed proximate a detecting region of said porous capillary column.

3. The method of claim 1, wherein said dispersing comprises dissolving the sample liquid mobile phase.

4. The method of claim 1, wherein said applying comprises applying the sample to porous capillary column with said at least one capture substrate comprising an antibody.

5. The method of claim 1, wherein said applying comprises applying the sample to porous capillary column with said at least one capture substrate comprising an antigen.

6. The method of claim 1, further comprising applying a differential pressure to said porous capillary column to effect said drawing.

7. The method of claim 1, wherein said drawing occurs without applying differential pressure to said porous capillary column.

8. The method of claim 7, wherein said drawing comprises capillary action induced by said matrix.

9. The method of claim 1, wherein said drawing comprises applying an electrical current across a length of said porous capillary column.

10. The method of claim 1, wherein said applying comprises applying the sample to said porous capillary column with said at least one capture substrate comprising at least one of an antibody and an antigen.

11. A method of identifying the presence of a constituent in a sample, comprising: providing the sample in a mobile phase;

applying the sample to a first end of a capillary column formed in a nonporous substrate, said capillary column comprising a matrix including the same material as said nonporous substrate;

drawing the sample across a flowfront through said capillary column and in contact with a stationary phase disposed at a selected location along said capillary column; and detecting binding of the constituent with said stationary phase at said selected location.

12. The method of claim 11, wherein said detecting comprises applying a detection reagent to at least said selected location and analyzing said detection reagent to determine whether the constituent is present.

13. The method of claim 12, wherein said analyzing comprises quantifying a change in said detection reagent.

14. The method of claim 11, wherein said detecting comprises determining an electrical characteristic of said selected location and comparing said electrical characteristic to an electrical characteristic of a control.

15. The method of claim 11, further comprising applying said stationary phase to said matrix.

16. The method of claim 15, wherein said applying said stationary phase is effected before said applying the sample.

17. The method of claim 11, wherein said applying comprises applying the sample to said capillary column with said stationary phase comprising an antibody.

18. The method of claim 11, wherein said applying comprises applying the sample to capillary column with said stationary phase comprising an antigen.

19. The method of claim 11, further comprising applying a differential pressure to capillary column to effect said drawing.

20. The method of claim 11, wherein said drawing occurs without applying differential pressure to said capillary column.

21. The method of claim 20, wherein said drawing comprises capillary action induced by said matrix.

22. The method of claim 11, wherein said drawing comprises applying an electrical current across a length of said capillary column.

23. The method of claim 11, wherein said applying the sample comprises applying the sample to said capillary column with said stationary phase comprising at least one of an antibody and an antigen.

\* \* \* \* \*